United States Patent
Jiang et al.

(10) Patent No.: US 11,813,073 B2
(45) Date of Patent: Nov. 14, 2023

(54) WOUND MULTIPLE SENSING METHOD AND WOUND MULTIPLE SENSING SYSTEM

(71) Applicant: Industrial Technology Research Institute, Hsinchu (TW)

(72) Inventors: Yue-Min Jiang, New Taipei (TW); Jian-Hong Liu, Kaohsiung (TW); Shang-Chih Hung, Hsinchu County (TW); Ho-Hsin Lee, Hsinchu (TW); Jian-Ren Chen, Hsinchu (TW); Min-Yi Hsieh, Taipei (TW); Ren-Guey Lee, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 326 days.

(21) Appl. No.: 17/133,352

(22) Filed: Dec. 23, 2020

(65) Prior Publication Data
US 2022/0192586 A1 Jun. 23, 2022

(51) Int. Cl.
*A61B 5/00* (2006.01)
*A61B 5/103* (2006.01)
(Continued)

(52) U.S. Cl.
CPC .............. *A61B 5/445* (2013.01); *A61B 5/107* (2013.01); *A61B 5/1032* (2013.01); *G16H 50/70* (2018.01); *A61B 2562/0271* (2013.01)

(58) Field of Classification Search
CPC ....... A61B 5/445; A61B 5/1032; A61B 5/107; A61B 2562/0271; A61B 5/01;
(Continued)

(56) References Cited

U.S. PATENT DOCUMENTS

| 7,395,216 B2 | 7/2008 | Rosenfeld et al. |
| 8,588,893 B2 | 11/2013 | Jaeb et al. |

(Continued)

FOREIGN PATENT DOCUMENTS

| CN | 105426167 A | 3/2016 |
| CN | 109069712 A | 12/2018 |

(Continued)

OTHER PUBLICATIONS

Altman et al., "Multiple linear regression", Nature Methods, 12, 1103-1104 (Year: 2015).*

(Continued)

*Primary Examiner* — Eric F Winakur
*Assistant Examiner* — Jonathan Drew Moroneso (57) ABSTRACT

A wound multiple sensing method, including: calculating the similarity between the current data sequence and each of the case-data sequences in each of the reference cases; selecting the case-data sequence which has the greatest similarity with the current data sequence, from the case-data sequences in each of the reference cases, to be a similar case-data sequence in each of the reference cases, wherein each similar case-data sequence corresponds to a similar case treatment; performing a multiple regression analysis using the similar case-data sequences and the similar case treatments to calculate a fitness function, wherein the dependent variable of the fitness function is a wound change; performing a parameter optimization algorithm using the current data sequence and the fitness function to calculate an optimal treatment which maximizes the wound change, and to calculate an expected wound change value that corresponds to the optimal treatment.

12 Claims, 8 Drawing Sheets

(51) Int. Cl.
*G16H 50/70* (2018.01)
*A61B 5/107* (2006.01)

(58) Field of Classification Search
CPC ...... A61B 5/1072; G16H 50/70; G16H 20/00; G16H 40/63
See application file for complete search history.

(56) References Cited

U.S. PATENT DOCUMENTS

| | | | |
|---|---|---|---|
| 10,636,144 B2 | 4/2020 | Gurevich | |
| 2001/0049609 A1 | 12/2001 | Girouard et al. | |
| 2006/0116904 A1* | 6/2006 | Brem | G16H 15/00 705/2 |
| 2010/0144690 A1* | 6/2010 | Ferguson | A61P 17/02 514/182 |
| 2017/0091410 A1 | 3/2017 | McCullough et al. | |
| 2017/0312161 A1* | 11/2017 | Johnson | A61H 31/006 |
| 2019/0392953 A1* | 12/2019 | Steuer | G16H 40/67 |
| 2020/0139024 A1* | 5/2020 | Pratt | A61M 1/85 |
| 2020/0193597 A1* | 6/2020 | Fan | A61B 5/7275 |
| 2020/0306426 A1* | 10/2020 | Rice | A61M 3/022 |
| 2020/0381087 A1* | 12/2020 | Ozeran | G06F 16/31 |
| 2021/0027897 A1* | 1/2021 | Rasochova | A61B 5/0077 |
| 2021/0290152 A1* | 9/2021 | Vogel | G16H 20/40 |
| 2023/0148951 A1* | 5/2023 | Thatcher | G06T 7/0012 382/128 |

FOREIGN PATENT DOCUMENTS

| | | |
|---|---|---|
| TW | 201247180 A1 | 12/2012 |
| TW | I689945 B | 4/2020 |

OTHER PUBLICATIONS

Todeschini et al., "Detecting "bad" regression models: multicriteria fitness functions in regression analysis", Science Direct, Analytica Chimica Acta, 515, 199-208 (Year: 2004).*

S Barone, A Paoli and A V Razionale, "Assessment of chronic wounds by three-dimensional optical imaging based on integrating geometrical, chromatic, and thermal data." Proc. IMechE, Jun. 2010, pp. 181-193, vol. 225.

* cited by examiner

| Wound Length | Wound Width | Wound Depth | ... | Roll-over Frequency | Dressing | Wound Care Skills | ... | Wound Change |
|---|---|---|---|---|---|---|---|---|
| 5 | 5 | 0.5 | ... | 2 | Gauze | Good | ... | 1.375 |
| 4 | 10 | 0.6 | ... | 5 | Silica Gel | Good | ... | 2.865 |
| 2.5 | 1.5 | 0.3 | ... | 3 | Acrylic Foam | Medium | ... | 2.275 |
| ... | ... | ... | ... | ... | ... | ... | ... | ... |

FIG. 3A

| | 301 | | | | 302 | | | 303 | |
|---|---|---|---|---|---|---|---|---|---|
| Wound Length | Wound Width | Wound Depth | ... | Roll-over Frequency | Dressing | Wound Care Skills | ... | Wound Length Change | Wound Width Change | Wound Depth Change |
| 5 | 5 | 0.5 | ... | 2 | Gauze | Good | ... | 0.6 | 0.3 | 0.2 |
| 4 | 10 | 0.6 | ... | 5 | Silica Gel | Good | ... | 0.4 | 0.5 | 0.2 |
| 2.5 | 1.5 | 0.3 | ... | 3 | Acrylic Foam | Medium | ... | 0.5 | 0.5 | 0.1 |
| ... | ... | ... | ... | ... | ... | ... | ... | ... | ... | ... |

WOUND MULTIPLE SENSING METHOD AND WOUND MULTIPLE SENSING SYSTEM

TECHNICAL FIELD

The technical field relates to a sensing method and a sensing system, and, in particular, to a wound multiple sensing method and a wound multiple sensing system.

BACKGROUND

According to official statistics, the global prevalence rate for aged people to develop arteriovenous ulcers and pressure sores is 6%, and the global prevalence rate for diabetes is 8.8%. These diseases often give chronic wounds to the patients that are difficult to heal, even over three months. It demonstrates that the need for remote wound care is considerable.

Ordinary nurses or caregivers, who often perform wound care, usually make decisions and treatments such as the simplest wound cleansing and disinfection only based on the current condition of the wound. However, such simple treatments only treat the symptoms rather than getting to the root of the problem, and often the wound may remain in the inflammation phase or the proliferative phase for a long time, and thereby delaying the healing of the wound. More than that, poor treatment decisions may cause the wound to fail to heal, increasing the risk of infections and necrosis, and finally resulting in septicemia or amputation.

Moreover, due to the complex and multifaceted features of care guidelines, it is difficult for ordinary nurses and caregivers to make well-considered decisions. When facing with complex situations, the doctrinal guidelines often cause the problems of unclear priorities or even paradoxes, thereby increasing the difficulty for ordinary nurses and caregivers to treat a patient's wound. Furthermore, it is quite perplexing to select an adequate dressing from a great variety of dressings. The expertise of professionals like Certified Wound, Ostomy and Continence Nurses, as well as other observations and suggestions relevant to wound conditions, are required.

Accordingly, there is a need for a wound multiple sensing method and a wound multiple sensing system, which can estimate the progress of wound healing and provide suggestions for treatments.

SUMMARY

An embodiment of this disclosure provides a wound multiple sensing method, including: calculating the similarity between the current data sequence and each of the case-data sequences in each of the reference cases; selecting the case-data sequence which has the greatest similarity with the current data sequence, from the case-data sequences in each of the reference cases, to be a similar case-data sequence in each of the reference cases, wherein each similar case-data sequence corresponds to a similar case treatment; performing a multiple regression analysis using the similar case-data sequences and the similar case treatments to calculate a fitness function, wherein the dependent variable of the fitness function is a wound change; performing a parameter optimization algorithm using the current data sequence and the fitness function to calculate an optimal treatment which maximizes the wound change, and to calculate an expected wound change value that corresponds to the optimal treatment.

In some embodiments, the method further includes: a first operation: estimating the expected data sequence using the current data sequence and the expected wound change value, wherein the expected data sequence comprises at least one size parameter; a second operation: performing the parameter optimization algorithm using the expected data sequence and the fitness function to calculate the next optimal treatment which maximizes the wound change, and the next expected wound change value corresponding to the next optimal treatment, and then estimating the next expected data sequence using the expected data sequence and the next expected wound change value; wherein the next expected data sequence is used as the new expected data sequence to iterate the second operation, until all of the size parameters in the next expected data sequence are calculated to be zero.

In some embodiments, the size parameter is the expected wound length, the expected wound width, and the expected wound depth.

In some embodiments, the method further includes: accumulating how many times the second operation is performed, until all of the size parameters in the next expected data sequence are calculated to be zero; adding one to the number of times that the operation has been performed, and then multiplying this by the cycle time during which the wound has been measured, so as to get the expected number of days required for the wound to heal.

In some embodiments, the wound change comprises three dimensions: a wound length change, a wound width change, and a wound depth change; and wherein the expected wound change value comprises the expected wound length change value, the expected wound width change value, and the expected wound depth change value.

In some embodiments, the method further includes: obtaining wound-tissue data in the multiple items of wound-observation data using a color sensor in a wound device; obtaining a wound surface area data in the multiple items of wound-observation data using a depth sensor in the wound device; obtaining wound-temperature data in the multiple items of wound-observation data using a temperature sensor in the wound device.

In some embodiments, each of the reference cases further comprises a characteristic record, a qualitative questionnaire record, and a treatment record; wherein the case-data sequences are created based on the characteristic record; and wherein the similar case treatments are created based on the qualitative questionnaire record and the treatment record.

An embodiment of this disclosure provides a wound multiple sensing system, including a processor to execute: calculating the similarity between the current data sequence and each of the case-data sequences in each of the reference cases; selecting the case-data sequence which has the greatest similarity with the current data sequence, from the case-data sequences in each of the reference cases, to be a similar case-data sequence in each of the reference cases, wherein each similar case-data sequence corresponds to a similar case treatment; performing a multiple regression analysis using the similar case-data sequences and the similar case treatments to calculate a fitness function, wherein the dependent variable of the fitness function is a wound change; performing a parameter optimization algorithm using the current data sequence and the fitness function to calculate an optimal treatment which maximizes the wound change, and to calculate an expected wound change value that corresponds to the optimal treatment.

In some embodiments, the processor further executes: a first operation: estimating the expected data sequence using the current data sequence and the expected wound change value, wherein the expected data sequence comprises at least one size parameter; a second operation: performing the parameter optimization algorithm using the expected data sequence and the fitness function to calculate the next optimal treatment which maximizes the wound change, and the next expected wound change value corresponding to the next optimal treatment, and then estimating the next expected data sequence using the expected data sequence and the next expected wound change value; wherein the next expected data sequence is used as the new expected data sequence to iterate the second operation, until all of the size parameters in the next expected data sequence are calculated to be zero.

In some embodiments, the processor further executes: accumulating how many times the second operation is performed, until all of the size parameters in the next expected data sequence are calculated to be zero; adding one to the number of times that the operation has been performed, and then multiplying this by the cycle time during which the wound has been measured, so as to get the expected number of days required for the wound to heal.

In some embodiments, the system further includes a wound device, which includes: a color sensor, configured to obtain wound-tissue data in the multiple items of wound-observation data; a depth sensor, configured to obtain a wound surface area data in the multiple items of wound-observation data; a temperature sensor, configured to obtain wound-temperature data in the multiple items of wound-observation data.

In some embodiments, the multiple items of wound-observation data includes the wound-tissue data, the wound surface area data, and the wound-temperature data; and the system further includes a wound device, which includes: a color sensor, configured to obtain wound-tissue data; a depth sensor, configured to obtain a wound surface area data; a temperature sensor, configured to obtain wound-temperature data.

The wound multiple sensing method and the wound multiple sensing system provided by this disclosure can estimate the progress of wound healing based on the current wound condition by referencing the similar cases accumulated in the past, and provide suggestions for treatments.

BRIEF DESCRIPTION OF THE DRAWINGS

The present disclosure can be more fully understood by reading the subsequent detailed description and examples with references made to the accompanying drawings, wherein.

DETAILED DESCRIPTION

The wound multiple sensing method provided by this disclosure is to compare the current condition of the patient's wound with multiple reference cases so as to shortlist multiple similar cases, and then to estimate the progress of wound healing based on the treatments and the healing process of the reference cases, and to provide suggestions for treatments.

According to an embodiment of the present application, each of the reference cases may include a plurality of evaluation results. The number of evaluation results depends on the time interval between the first time the wound is sensed and the last time it is measured, at which point it will be completely healed, as well as the frequency (or cycle time) at which it is sensed. For example, let us assume that the wound completely heals on the $18^{th}$ day since the first day the wound was measured. If the frequency during which the wound has been measured during the 18 days is once a day, then there will be 18 evaluation results. If the frequency during which the wound has been measured during the 18 days is once per three days, then there will be 6 evaluation results. Each of the evaluation results further includes a characteristic record, a qualitative questionnaire record, and a treatment record.

The characteristic record may include multiple items of wound-observation data, such as the wound position (e.g., back, ankle, wrist, etc.), the wound length, the wound width, the wound depth, the wound surface area, the amount of effusion, the effusion's property, the effusion's color, the wound temperature, the wound tissue, etc. In some embodiments, a wound device may be used to obtain multiple items of wound-observation data in the characteristic record. For example, the color sensor in the wound device may be used to obtain the wound-tissue data, the depth sensor in the wound device may be used to obtain the wound surface area data, and the temperature sensor in the wound device may be used to obtain the wound-temperature data.

The qualitative questionnaire record may include, for example, the environment for bedfast patients (e.g., the frequency and the way of bed-making), the roll-over skills (e.g., the frequency and the way of changing dressing), and the physiologic observation (e.g., visual evaluation for the wound condition, symptoms of fever or chills, and the evaluation for other physiologic conditions). The treatment record may include, for example, the dressing's type (e.g., gauze, silica gel, acrylic foam, etc.), the person to be health educated (e.g., a caregiver or a family member), and the content of health education (e.g., bed-making skills, wound care skills, roll-over skills, etc.). In some embodiments, the qualitative questionnaire record and the treatment record may be filled in by the caregiver or the patient, based on their own experience, cognition, and feelings.

Figure 1:
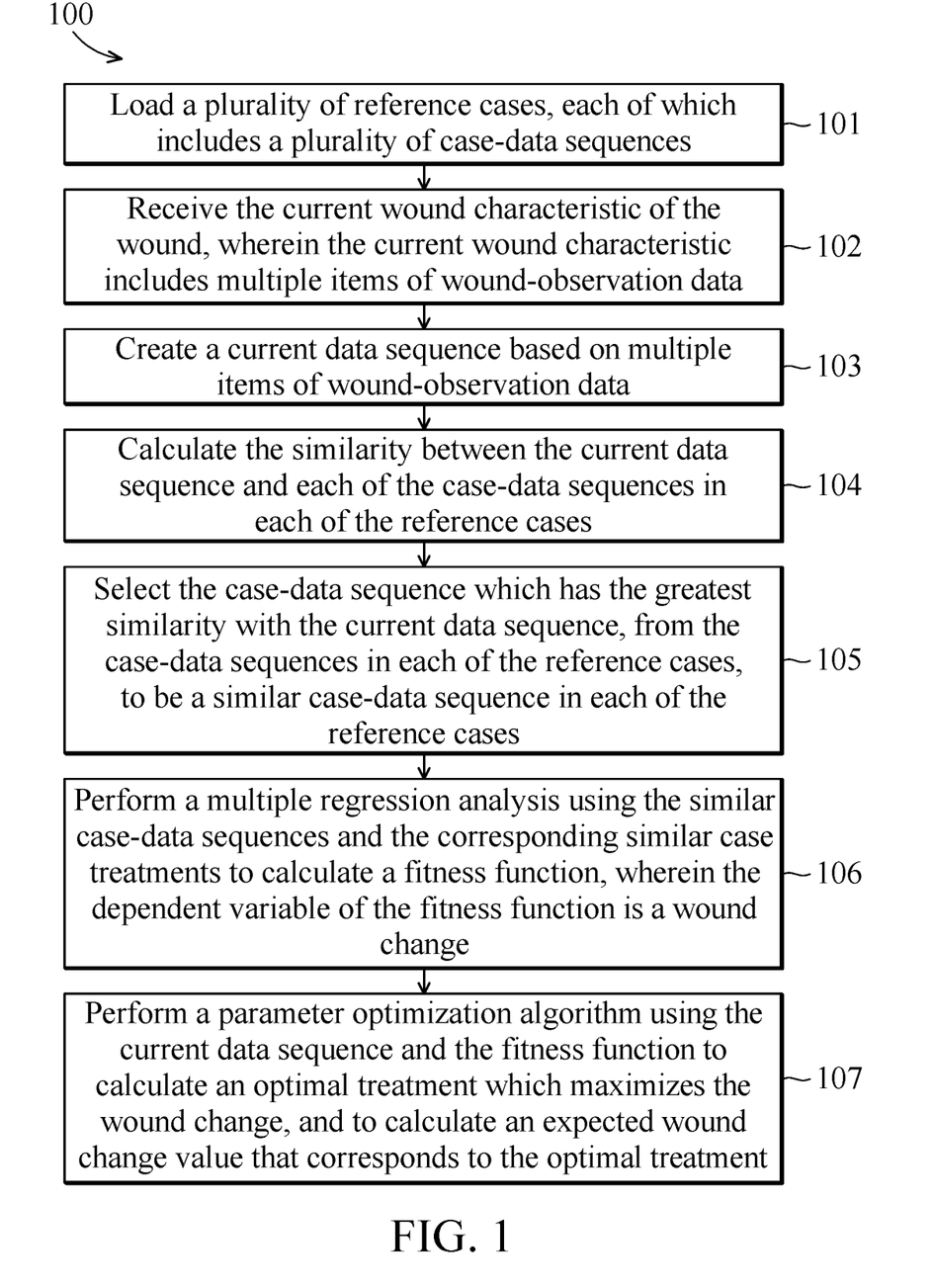
FIG. 1 illustrates the flow diagram of a method 100, according to an embodiment of the present application.

FIG. 1 illustrates the flow diagram of a method 100, according to an embodiment of the present application. As shown in FIG. 1, the method 100 includes the operations 101-107. In the operation 101, load a plurality of reference cases, each of which includes a plurality of case-data sequences. Then, the method 100 proceeds to the operation 102.

According to an embodiment of the present application, as described above, the number of reference cases loaded in the operation 101 depends on the time interval starting from the first time the wound is measured to the time needed for the wound to completely heal, as well as the cycle time during which the wound has been measured during the time interval. The plurality of case-data sequences included in each of the reference cases are created based on multiple items of wound-observation data in the characteristic record collected each time.

Figure 2:
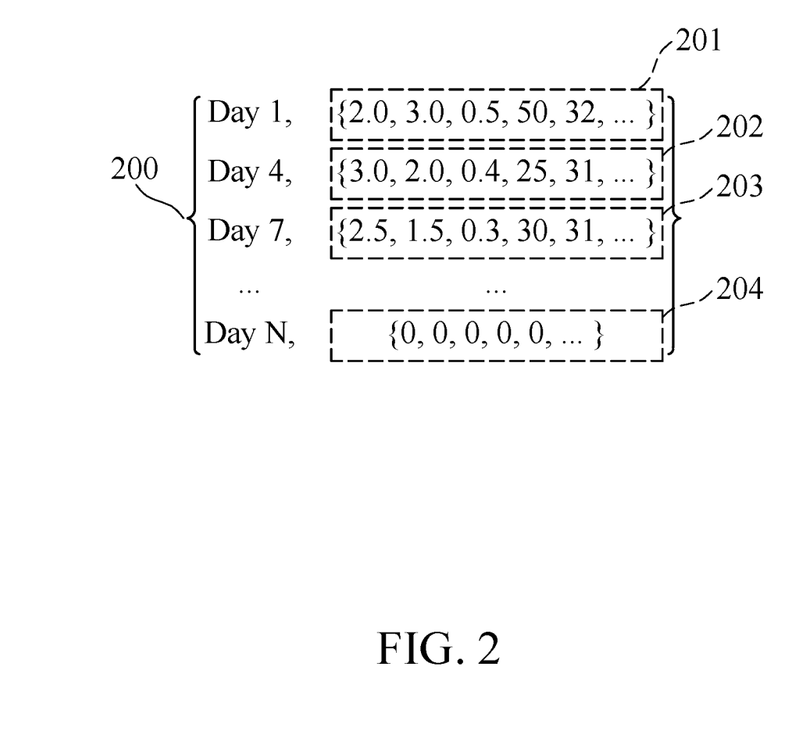
FIG. 2 provides an example for a reference case 200, according to an embodiment of the present application.

FIG. 2 provides an example for a reference case 200, according to an embodiment of the present application. As shown in FIG. 2, the reference case 200 includes a plurality of case-data sequences, such as case-data sequence 201, case-data sequence 202, case-data sequence 203, and case-data sequence 204. In the disclosed example, it is assumed that the frequency (or cycle time) during which the wound has been measured during the time interval starting from the first time the wound is measured (i.e., the "Day 1" in FIG. 2) to the time point at which the wound to completely heal (i.e., the "Day N" in FIG. 2) is once per three days. Case-data sequence 201, case-data sequence 202, case-data sequence 203, and case-data sequence 204 are created based on multiple items of wound-observation data in the characteristic record collected on Day 1, Day 2, Day 7, and Day N respectively. For example, The case-data sequence 201 {2.0, 3.0, 0.5, 50, 32, . . . } may represent that the wound length, the wound width, the wound depth, the amount of effusion, the wound temperature and so on, which are collected on Day 1, are 2.0, 3.0, 0.5, 50, 32 and so on respectively. The case-data sequence 202 {3.0, 2.0, 0.4, 25, 31, . . . } may represent that the wound length, the wound width, the wound depth, the amount of effusion, the wound temperature and so on, which are collected on Day 4, are 3.0, 2.0, 0.4, 25, 31 and so on respectively. The case-data sequence 203 {2.5, 1.5, 0.3, 30, 31, . . . } may represent that the wound length, the wound width, the wound depth, the amount of effusion, the wound temperature and so on, which are collected on Day 7, are 2.5, 1.5, 0.3, 30, 31 and so on respectively. All items in the case-data sequence 201 are zero, representing that the wound is measured to completely heal on Day N.

Back to FIG. 1, the method 100 now proceeds to the operation 102. In the operation 102, receive the current wound characteristic of the wound, wherein the current wound characteristic includes multiple items of wound-observation data. Then, the method 100 proceeds to the operation 103.

According to an embodiment of the present application, the multiple items of wound-observation data included in the current wound characteristic may be corresponding to the multiple items of wound-observation data included in the characteristic record of the reference cases. That is to say, the current wound characteristic may include multiple items of wound-observation data, such as the wound position (e.g., back, ankle, wrist, etc.), the wound length, the wound width, the wound depth, the wound surface area, the amount of effusion, the effusion's property, the effusion's color, the wound temperature, the wound tissue, etc. Similarly, in some embodiments, a wound device may be used to obtain multiple items of wound-observation data in the current characteristics. For example, the color sensor in the wound device may be used to obtain the wound-tissue data, the depth sensor in the wound device may be used to obtain the wound surface area data, and the temperature sensor in the wound device may be used to obtain the wound-temperature data.

Back to FIG. 1, the method 100 now proceeds to the operation 103. In the operation 103, create a current data sequence based on multiple items of wound-observation data. Then, the method 100 proceeds to the operation 104.

According to an embodiment of the present application, the recorded form of the current data sequence is of the same as the case-data sequence of the reference cases. That is to say, the current data sequence may be recorded in form of $\{x_1, x_2, x_3, x_4, x_5, \ldots\}$, just like the case-data sequence 201, the case-data sequence 202, or the case-data sequence 203.

In some embodiments, in the operation 103, the multiple items of wound-observation data may go through a standardization process first, and then the standardized wound-observation data is used to create the current data sequence. Since standardization is a known technique for data processing, its details are not described herein again. In some embodiments, the range for each items of wound-observation data may be converted into a specific range of value (e.g., 0-5) through the computation using some mathematical functions.

Back to FIG. 1, the method 100 now proceeds to the operation 104. In the operation 104, calculate the similarity between the current data sequence and each of the case-data sequences in each of the reference cases. For example, calculate the similarity between the current data sequence and the case-data sequence 201 on Day 1, the similarity between the current data sequence and the case-data sequence 202 on Day 4, the similarity between the current data sequence and the case-data sequence 203 on Day 7 and so on in the reference cases in FIG. 2. Also, calculate the similarity between the current data sequence and each case-data sequence in each of other reference cases. Then, the method 100 proceeds to the operation 105.

In some embodiments, the calculation of similarity is to localize the current data sequence and each case-data sequence in a coordinate system, and them to calculate the Euclidean distance between them. To be specific, calculate the sum of square of the difference values between the current data sequence and a case-data sequence, and then calculate the square root of the sum of square so as to get the Euclidean distance between the current data sequence and the case-data sequence. For example, assuming that the current data sequence is $\{x_1, x_2, x_3, \ldots, x_n\}$ and an exemplary case-data sequence is $\{y_1, y_2, y_3, \ldots, y_n\}$, then the Euclidean distance between the current data sequence and the exemplary case-data sequence is $\sqrt{\Sigma_{i=1}^{n}(x_i-y_i)^2}$. It should be appreciated that the shorter the Euclidean distance, the greater the similarity.

Back to FIG. 1, the method now proceeds to the operation 105. In the operation 105, select the case-data sequence which has the greatest similarity (e.g., the shortest Euclidean distance) with the current data sequence, from the case-data sequences in each of the reference cases, to be a similar case-data sequence in each of the reference cases. For example, select the case-data sequence which has the greatest similarity with the current data sequence, from all the case-data sequences in each of the reference cases in FIG. 2, to be a similar case-data sequence in the reference case 200. Also, perform the same operation as described above on other reference cases, so as to get multiple similar case-data sequences. Then, the method 100 proceeds to the operation 106.

According to an embodiment of the present application, each of the similar case-data sequences corresponds to a similar case treatment. The similar case treatment is created based on the qualitative questionnaire record and the treatment record corresponding to the characteristic record which is used to create the similar case-data sequence. For example, assuming that the similar case-data sequence in the reference case 200 is the case-data sequence 203, which means that among the multiple evaluation results in the reference case 200, the wound characteristic on Day 7 is the most similar to the current wound characteristic, and thus the similar case treatment is created based on the qualitative questionnaire record and the treatment record on Day 7.

Back to FIG. 1, the method 100 now proceeds to the operation 106. In the operation 106, perform a multiple regression analysis using the similar case-data sequences and the corresponding similar case treatments to calculate a fitness function, wherein the dependent variable of the fitness function is a wound change. Then, the method 100 proceeds to the operation 107.

Figure 3A:
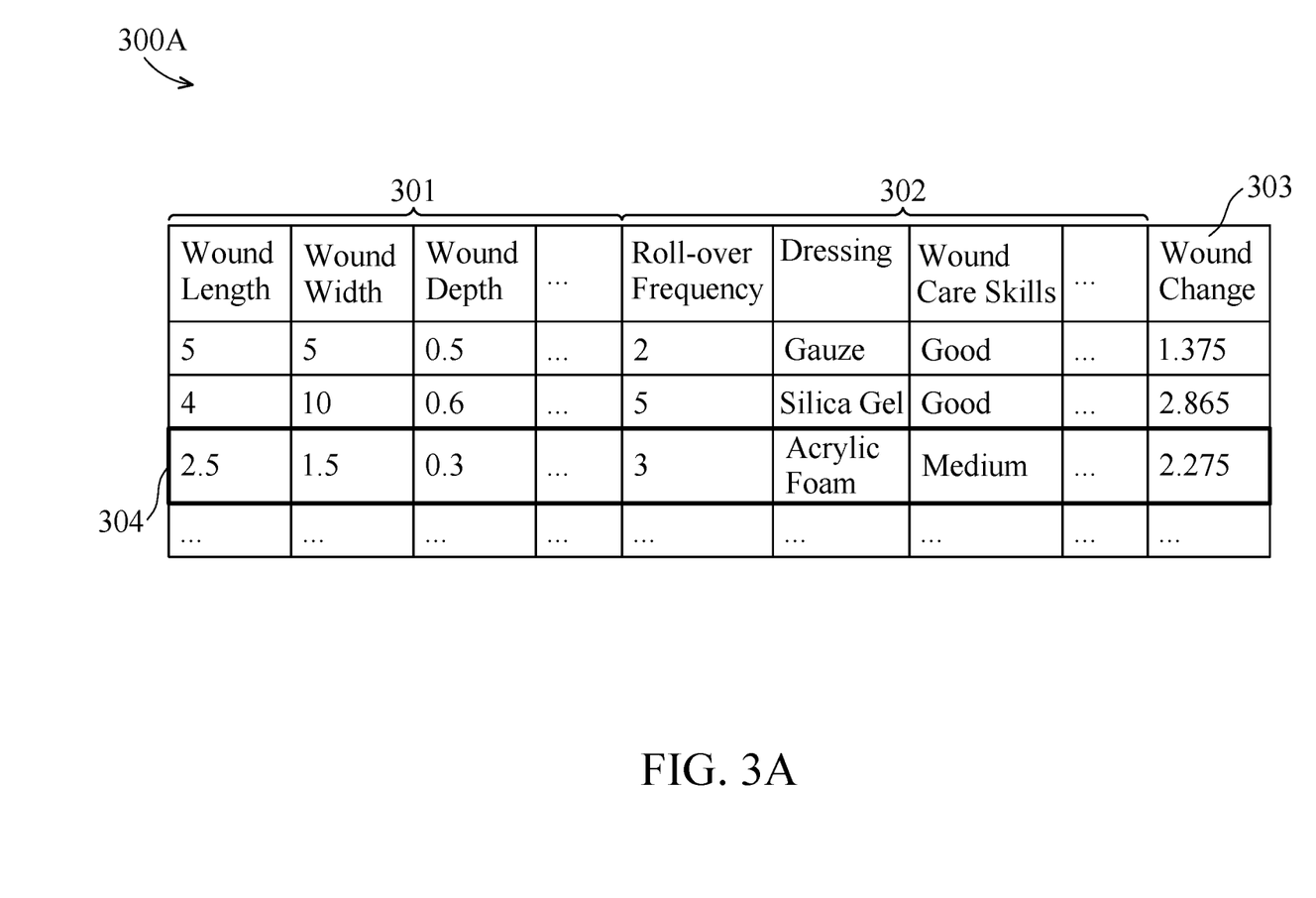
FIG. 3A provides an example for an input data 300A which is required for multiple regression analysis, according to an embodiment of the present application.

FIG. 3A provides an example for an input data 300A which is required for multiple regression analysis, according to an embodiment of the present application. As shown in FIG. 3A, the input data 300A includes a similar case-data sequence 301, a similar case treatment 302, and the wound change 303 from multiple reference cases. The wound change 303 is gotten by comparing the difference the similar case-data sequence in each of the reference cases and its previous one of the case-data sequences. For example, assuming that the similar case-data sequence in the reference case 200 is the case-data sequence 203, and that the row 304 in FIG. 3A is the combination of the similar case-data sequence (i.e., the case-data sequence 203), the similar case treatment (i.e., the case treatment created based on the qualitative questionnaire record and the treatment record on Day 7), and the wound change. Thus, the wound change in row 304 is gotten by comparing the difference between the case-data sequence 203 and its previous one of the case-data sequences (i.e., the case-data sequence 202). In a variety of embodiments, the wound change may be, for example, a wound length change, a wound width change, a change in wound surface area, or a wound volume change. In the example as shown in FIG. 3A, the wound change means the wound volume change. For example, the wound change value in row 304 is the difference value between the wound volume indicated by the reference data sequence 203 and the wound volume indicated by the reference data sequence 202. The calculation is as follows:

$$3.0*2.0*0.4-2.5*1.5*0.3=2.275$$

Back to FIG. 1, the method 100 now proceeds to the operation 107. In the operation 107, perform a parameter optimization algorithm using the current data sequence and the fitness function to calculate an optimal treatment which maximizes the wound change, and to calculate an expected wound change value that corresponds to the optimal treatment. The optimal treatment and the expected wound change value may be displayed on a display device in order to provide suggestions for wound treatments to the caregiver.

According to an embodiment of the present application, the parameter optimization algorithm uses the current data sequence and the fitness function as input. The purpose of the parameter optimization algorithm is to find a best case treatment, that is, the best combination of the data of the qualitative questionnaire record and the data of the treatment record (e.g., the combination of the roll-over frequency, the dressing, the wound care skills, etc.), which maximizes the wound change (e.g., a wound length change, a wound width change, a change in wound surface area, or a wound volume change). Thus, the maximized wound change value is the expected wound change value. For example, assuming that there is a first treatment "the roll-over frequency is 3, the dressing is acrylic foam, the wound care skills are good . . . " corresponding to a wound change value 3.5. If the parameter optimization algorithm determines that the wound change value cannot be greater than 3.5 by changing the first treatment, then the first treatment is the optimal treatment, and the expected wound change value corresponding to the first treatment is 3.5. In some embodiments, the parameter optimization algorithm may be one of a variety of heuristic algorithms, such as a genetic algorithm (GA), an ant colony optimization, or a particle swarm optimization (PSO). The present disclosure is not limited thereto.

Figure 3B:
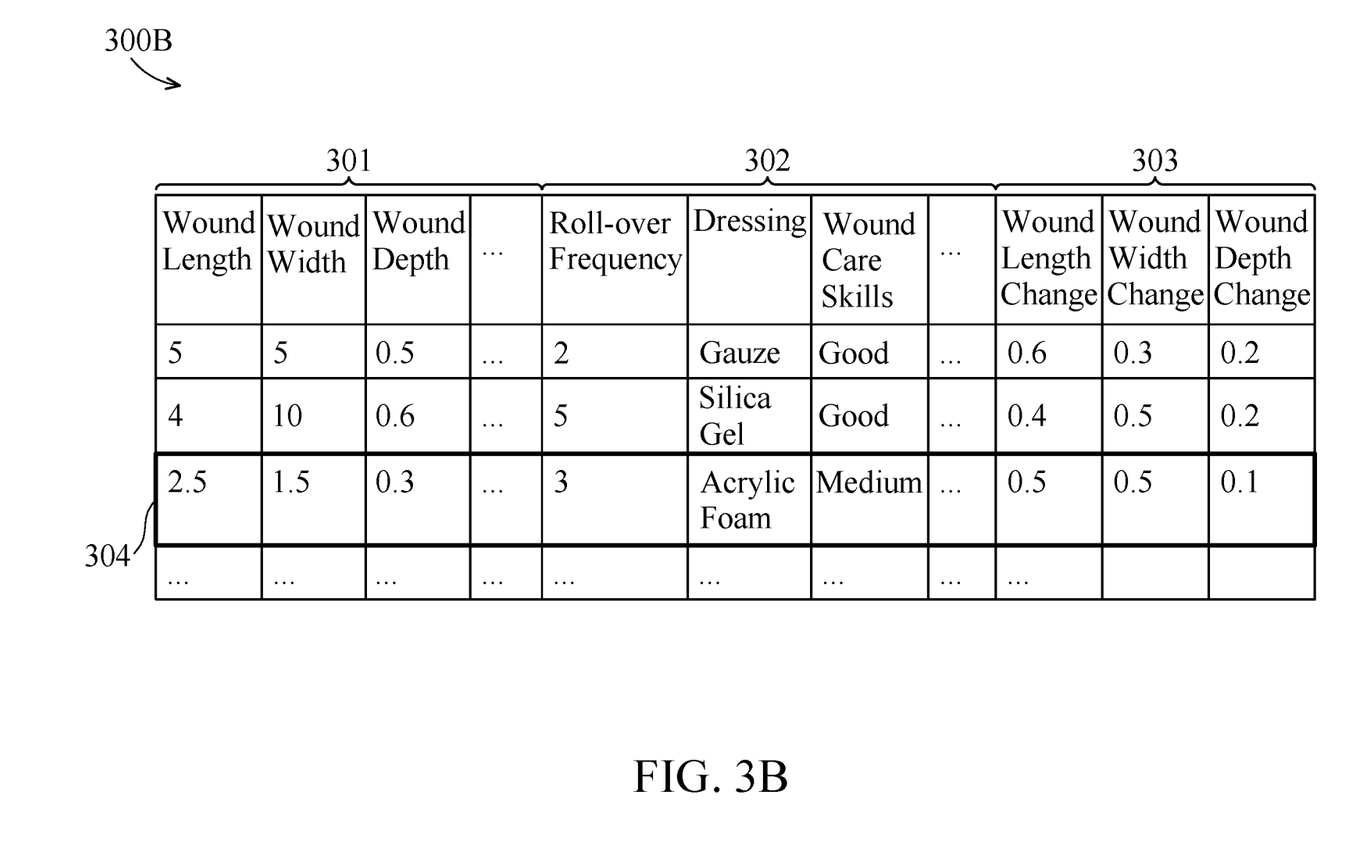
FIG. 3B provides an example for an input data 300B which is required for multiple regression analysis, according to an alternative embodiment of the present application.

FIG. 3B provides an example for an input data 300B which is required for multiple regression analysis, according to an embodiment of the present application. The difference between FIG. 3B and FIG. 3A is that the wound change further includes three dimensions: the wound length change, the wound width change, and the wound depth change. This means that the fitness function calculated by performing multiple regression analysis has three dependent variables: the wound length change, the wound width change, and the wound depth change. In the disclosed example, the wound length change value (0.5) in row 304 is the difference value between the wound length (2.5) indicated by the case-data sequence 203 and the wound length (3.0) indicated by the case-data sequence 202. The calculation is as follows:

$$3.0-2.5=0.5$$

The wound width change value (0.5) in row 304 is the difference value between the wound width (1.5) indicated by the case-data sequence 203 and the wound width (2.0) indicated by the case-data sequence 202. The calculation is as follows:

$$2.0-1.5=0.5$$

The wound depth change value (0.1) in row 304 is the difference value between the wound depth (0.3) indicated by the case-data sequence 203 and the wound depth (0.4) indicated by the case-data sequence 202. The calculation is as follows:

$$0.4-0.3=0.1$$

In the alternative embodiment as shown in FIG. 3, the fitness function has three dependent variables: the wound length change, the wound width change, and the wound depth change, so the expected wound change value output by the parameter optimization algorithm is a combination of the expected wound length change value, the expected wound width change value, and the expected wound depth change value. Additionally, the target to be maximized by the parameter optimization algorithm is the wound volume change. For example, assuming that the current data sequence indicates that currently the wound length is 10, the wound width is 5, and the wound depth is 0.5, and further assuming that there is a second treatment "the roll-over frequency is 3, the dressing is acrylic foam, the wound care skills are good . . . " corresponding to a wound length change value 2, a wound width change value 1, and a wound depth change value 0.1, then the wound volume change corresponding to the second treatment is: the product of the current wound length, the current wound width, and the current wound depth, minus the product of "the current wound length minus the wound length change value", "the current wound width minus the wound width change value", and "the current wound depth minus the wound depth change value". The calculation is as follows:

$$10*5*0.5-(10-2)*(5-1)*(0.5-0.1)=12.2$$

If the parameter optimization algorithm determines that the wound volume change value cannot be greater than 12.2 by changing the second treatment, then the second treatment is the optimal treatment. The expected wound length change value, the expected wound width change value, and the expected wound depth change value that are corresponding to the second treatment are 2, 1 and 0.1 respectively.

Figure 4:
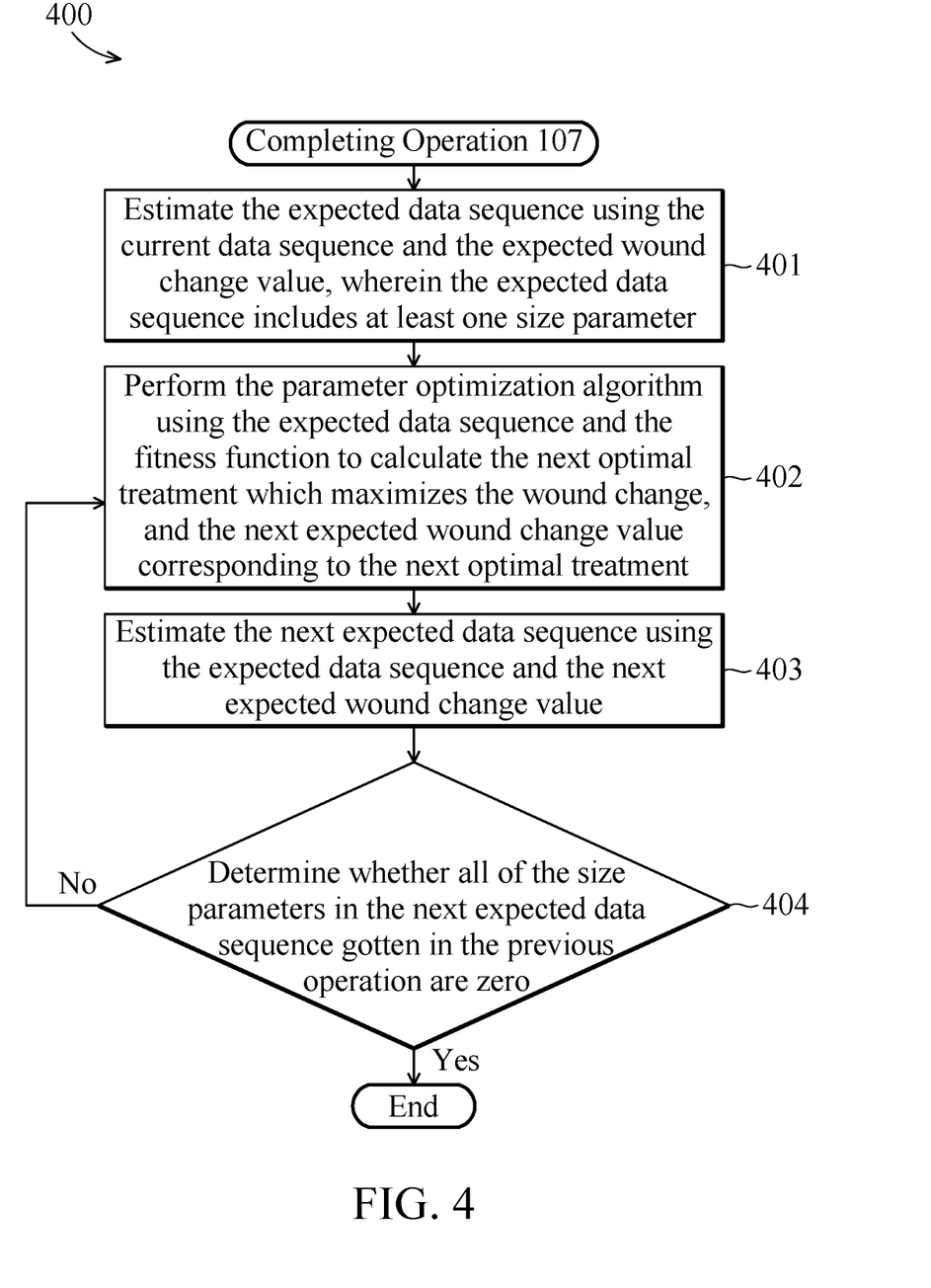
FIG. 4 illustrates the flow diagram of a method 400, according to an embodiment of the present application.
Figure 5:
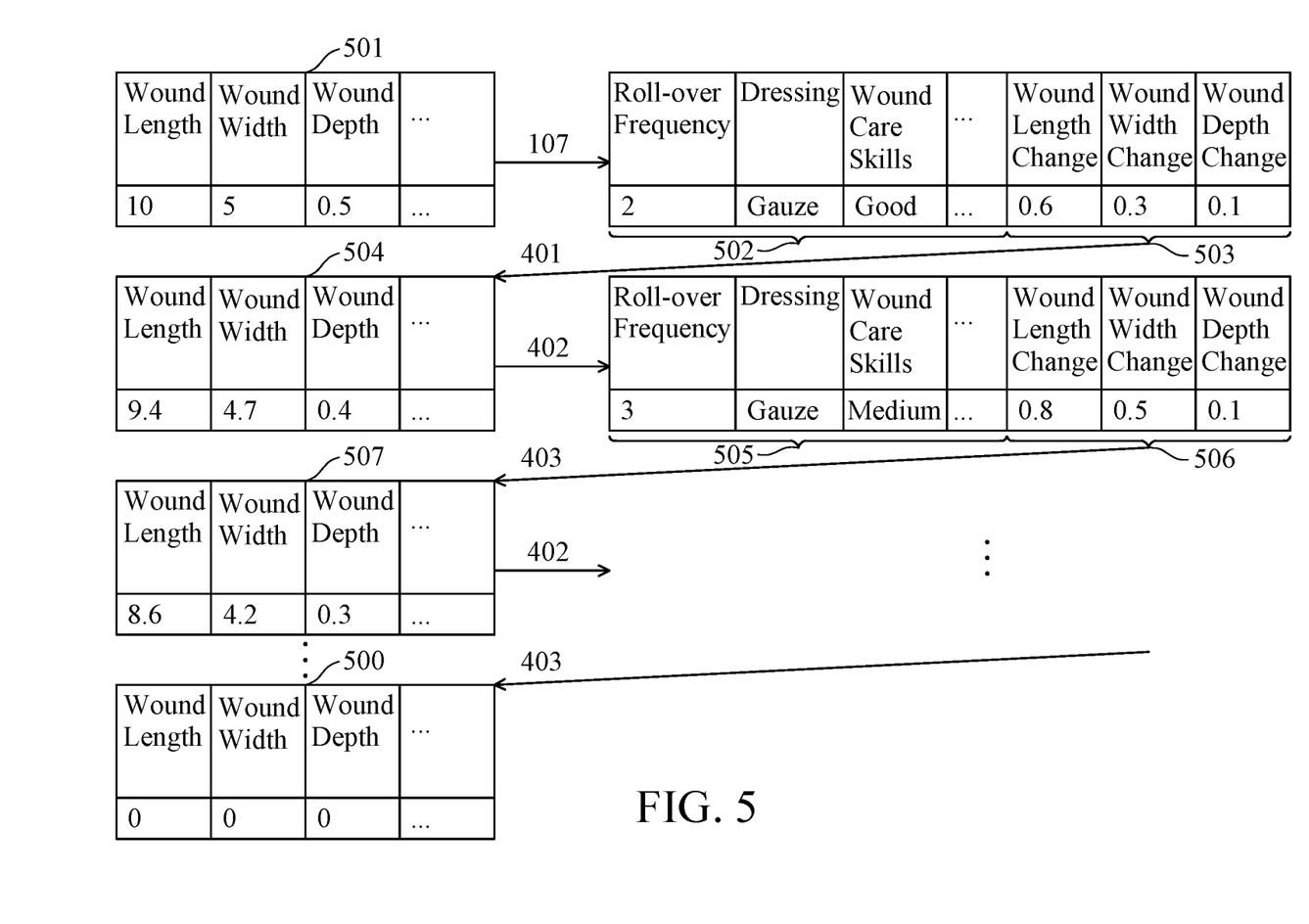
FIG. 5 provides an example for a series of optimal treatments, a series of expected wound change value, and a series of expected data sequences which are produced during performing the method 400, according to an alternative embodiment of the present application.

In some embodiments, after completing the operation 107 in the method 100, proceed to perform a method 400. FIG. 4 illustrates the flow diagram of a method 400, according to an embodiment of the present application. FIG. 5 provides an example for a series of optimal treatments, a series of expected wound change value, and a series of expected data sequences which are produced during performing the method 400, according to an alternative embodiment of the present application. To better understand this disclosure, the descriptions as follows will require cross-referencing FIG. 4 and FIG. 5. It should be appreciated that the value in each forms in FIG. 5 is only for example to better describe the embodiments of this disclosure, and not intended to limit the present disclosure.

As shown in FIG. 4, the method 400 includes the operations 401-404. The method 400 starts from the completion of the operation 107, and then proceeds to the operation 401. In the operation 401, estimate the expected data sequence using the current data sequence and the expected wound change value, wherein the expected data sequence includes at least one size parameter. Then, the method 400 proceeds to the operation 402.

According to an embodiment of the present application, the expected data sequence is the result of the current data sequence minus the expected wound change value. In some embodiments, the size parameter included in the expected data sequence may be the expected wound length, the expected wound width, the expected wound depth, or a combination thereof.

In an alternative embodiment, the fitness function has three dependent variables: the wound length change, the wound width change, and the wound depth change, so the expected wound change value output by the parameter optimization algorithm includes the expected wound length change value, the expected wound width change value, and the expected wound depth change value, and the size parameters included in the expected data sequence are the expected wound length, the expected wound width, and the expected wound depth. In FIG. 5, for example, the current data sequence 501 created based on the wound condition at the current point of time indicates that the wound length is 10, the wound width is 5, and the wound depth is 0.5. After completing the operation 107, the optimal treatment 502 and the expected wound change value 503 are gotten. The expected wound change value 503 includes the expected wound length change value (0.6), the expected wound width change value (0.3), and the expected wound depth change value (0.1). Then, through the operation 401, subtract the expected wound length change value (0.6), the expected wound width change value (0.3), and the expected wound depth change value (0.1) in the expected wound change value 503 from the wound length (10), the wound width (5), and the wound depth (0.5) indicated by the current data sequence 501 respectively, and thereby get the expected data sequence 504. The calculation is as follows:

The expected wound length in the expected data sequence 504: 10−0.6=9.4

The expected wound width in the expected data sequence 504: 5−0.3=4.7

The expected wound depth in the expected data sequence 504: 0.5−0.1=0.4

Back to FIG. 4, the method 400 now proceeds to the operation 402. In the operation 402, perform the parameter optimization algorithm using the expected data sequence and the fitness function to calculate the next optimal treatment which maximizes the wound change, and the next expected wound change value corresponding to the next optimal treatment. Then, the method 400 proceeds to the operation 403.

According to an embodiment of the present application, the parameter optimization algorithm and the fitness function used in the operation 402 and the operation 407 are alike, expect that the operation 107 is to search for the optimal treatment based on the current data sequence, while the operation 402 is to search for the optimal treatment based on the expected data sequence. Taking FIG. 5 for example, in this alternative embodiment, after completing the operation 402 on the expected data sequence 504, the next optimal treatment (i.e., the optimal treatment 505) and the next expected wound change value (i.e., the expected wound change value 506) are gotten. The expected wound change value 506 includes the expected wound length change value (0.8), the expected wound width change value (0.5), and the expected wound depth change value (0.1).

Back to FIG. 4, the method 400 now proceeds to the operation 403. In the operation 403, estimate the next expected data sequence using the expected data sequence and the next expected wound change value. Then, the method 400 proceeds to the operation 404.

According to an embodiment of the present application, the way of estimating the expected data sequence in the operation 403 and the operation 401 are alike, expect that the operation 401 is to subtract the expected wound change value from the current data sequence, while the operation 403 is to subtract the next expected wound change value from the expected data sequence. Taking FIG. 5 for example, in this alternative embodiment, the operation 403 is to subtract the next expected wound change value, which is gotten after completing the operation 402, from the expected data sequence 504, so as to get the next expected data sequence (i.e., the expected data sequence 507). The calculation is as follows:

The expected wound length in the expected data sequence 507: 9.4−0.8=8.6

The expected wound width in the expected data sequence 507: 4.7−0.5=4.2

The expected wound depth in the expected data sequence 507: 0.4−0.1=0.3

Back to FIG. 4, the method 400 now proceeds to the operation 404. In the operation 404, determine whether all of the size parameters in the next expected data sequence gotten in the previous operation are zero. If not, then the method 400 returns to the operation 402. If yes, it means that the wound is expected to completely heal, so the method 400 is ended.

Taking FIG. 5 for example, in this alternative embodiment, the expected data sequence 507 will further go through the operation 402, the operation 403, and the operation 404, in order to get the further next expected data sequence. Constantly iterate the operation 402, the operation 403, and the operation 404 in this way, until the wound is expected to heal (e.g., the expected wound length, the expected wound width, and the expected wound depth in the expected data sequence 500 are all zero, as shown in FIG. 5).

According to an embodiment of the present application, a series of optimal treatments (e.g., the optimal treatment 502, the optimal treatment 505, and so on in FIG. 5), a series of expected wound change values (e.g., the expected wound change value 503, the expected wound change value 506, and so on in FIG. 5), and a series of expected data sequences (e.g., the expected data sequence 504, the expected data sequence 507, and so on in FIG. 5) produced during performing the method 400 may all be displayed on a display device, so as to provide suggestions for wound treatments. In some embodiments, the number of times for performing the operation 402 and the operation 403 during performing the method 400 may be accumulated, and then the accumulated number of times is plus by one, and then multiplied by the frequency (or cycle time) during which the wound has been measured, so as to get the expected number of days required for the wound to heal. For example, assuming that the frequency during which the wound has been measured is once per three days, and the wound is expected to heal after performing the operation 402 and the operation 403 for 8 times, then the expected number of days required for the wound to heal is 27. The calculation is as follows:

(8+1)*3=27

Figure 6A:
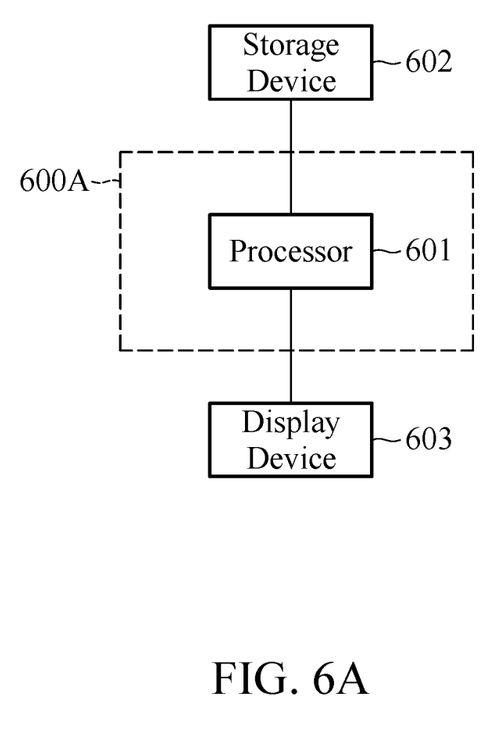
FIG. 6A illustrates the block diagram of a computing environment in which a system 600A is located, according to an embodiment of the present application.

FIG. 6A illustrates the block diagram of a computing environment in which a system 600A is located, according to an embodiment of the present application. As shown in FIG. 6A, the system 600A includes a processor 601. The processor 601 may connect to a storage device 602 with or without wires to load the reference cases stored in the storage device 602, so as to perform the method 100 and the method 400 as described above. The processor 601 may also connect to a display device 603 with or without wires, so that a series of optimal treatments, a series of expected wound change values, and a series of expected data sequences may be displayed on the display device 603, so as to provide suggestions for wound treatments to the caregiver. It should be appreciated that in FIG. 6A, though the storage device 602 is not included in the system 600A, but in some embodiments, the system 600A may further include the storage device 602. Similarly, in FIG. 6A, though the display device 603 is not included in the system 600A, but in some embodiments, the system 600A may further include the display device 603.

The processor 601 may be any device used for executing instructions, such as a CPU, a microprocessor, a controller, a microcontroller, or a state machine. The present disclosure is not limited thereto. The storage device 602 may be any device used for storing data, such as a disk drive, an optical storage device, and a solid-state storage device such as a RAM, a ROM, a removable media device, a memory card, or a flash memory card. The present disclosure is not limited thereto. The display device 603 may be any device used for displaying texts and images, such as an LCD device, an LED device, an OLED device, or a plasma display device. The present disclosure is not limited thereto.

Figure 6B:
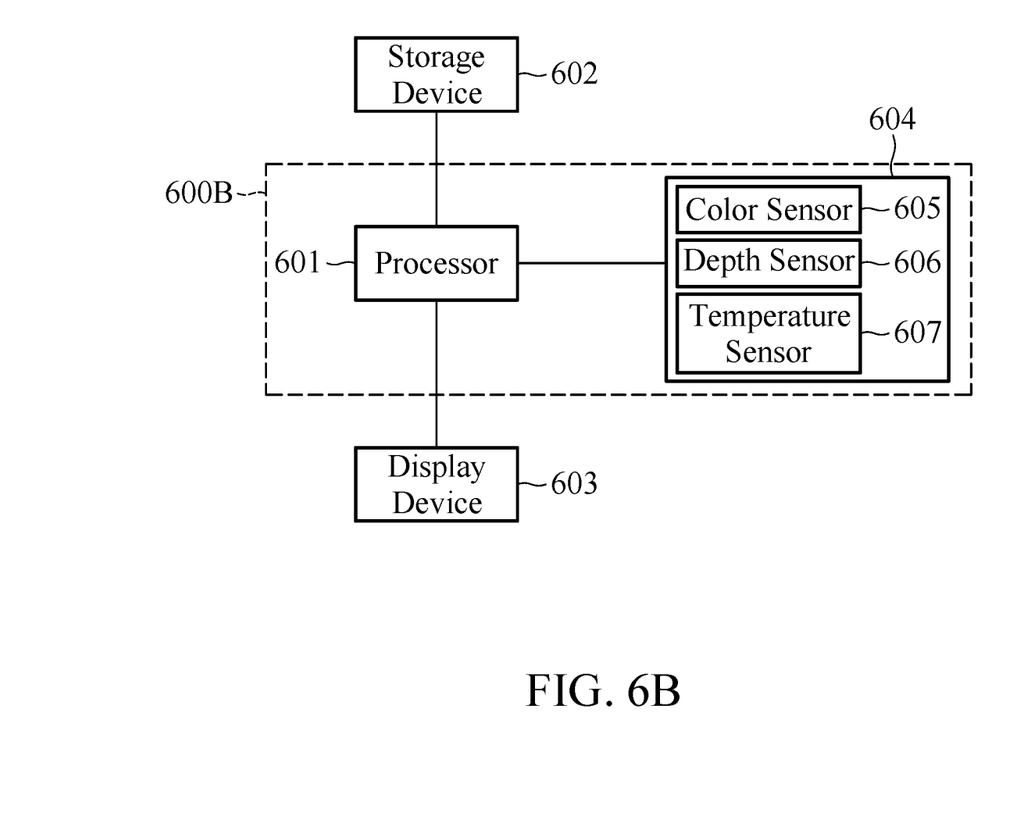
FIG. 6B illustrates the block diagram of a computing environment in which a system 600B is located, according to another embodiment of the present application.

FIG. 6B illustrates the block diagram of a computing environment in which a system 600B is located, according to another embodiment of the present application. As compared to the system 600A in FIG. 6A, the system 600B further include a wound device 604. The wound device 604 includes a color sensor 605, a depth sensor 606, and a temperature sensor 607, configured to obtain the wound-tissue data, the wound surface area data, and the wound-temperature data respectively. The wound device 604 may connect to the processor 601 with or without wires to transfer the obtained multiple items of wound-observation data to the processor 601, and thus the processor 601 may create the current data sequence based on these wound-observation data. It should be appreciated that in FIG. 6B, though the storage device 602 is not included in the system 600B, but in some embodiments, the system 600B may further include the storage device 602. Similarly, in FIG. 6B, though the display device 603 is not included in the system 600B, but in some embodiments, the system 600B may further include the display device 603. Furthermore, though the system 600B includes the processor 601 and the processor 604, yet the present disclosure does not limit to whether the processor 601 and the processor 604 are configured in the same electronic device.

In conclusion, the wound multiple sensing method and the wound multiple sensing system provided by this disclosure can estimate the progress of wound healing based on the current wound condition by referencing the similar cases accumulated in the past, and provide suggestions for treatments.

Ordinal terms used in the claims, such as "first," "second," "third," and so on, are used to modify the elements appearing in the claims, and do not imply any prioritization, precedence relation, or a component is higher than the other component, or the chronological order in which the method steps are performed. The intention is to make a distinction between elements with the same name.

The above paragraphs are described with multiple embodiments. Obviously, the teachings of the specification may be performed in multiple ways. Any specific structure or function disclosed in examples is only a representative situation. According to the teachings of the specification, it should be noted by those skilled in the art that any embodiment disclosed may be performed individually, or that more than two embodiments could be combined and performed.

While the invention has been described by way of example and in terms of the alternative embodiments, it should be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A wound multiple sensing method, executed by a processor, the method comprising:
loading a plurality of reference cases, wherein each of the reference cases comprises a plurality of case-data sequences;
receiving a current wound characteristic of a wound, wherein the current wound characteristic comprises multiple items of wound-observation data;
creating a current data sequence based on the multiple items of wound-observation data;
calculating the similarity between the current data sequence and each of the case-data sequences in each of the reference cases;
selecting the case-data sequence which has the greatest similarity with the current data sequence, from the case-data sequences in each of the reference cases, to be a similar case-data sequence in each of the reference cases, wherein each similar case-data sequence is associated with a corresponding similar case treatment;
performing a multiple regression analysis using the similar case-data sequences and the similar case treatments to derive a fitness function, wherein the dependent variable of the fitness function is a wound change;
performing a heuristic algorithm using the current data sequence and the fitness function to calculate an optimal treatment which maximizes the wound change, and to calculate an expected wound change value that corresponds to the optimal treatment;

obtaining wound-tissue data in the multiple items of wound-observation data using a color sensor in a wound device;

obtaining wound surface area data in the multiple items of wound-observation data using a depth sensor in the wound device; and obtaining wound-temperature data in the multiple items of wound-observation data using a temperature sensor in the wound device.

2. The wound multiple sensing method as claimed in claim 1, further comprising:

a first operation: estimating an expected data sequence using the current data sequence and the expected wound change value, wherein the expected data sequence comprises at least one size parameter;

a second operation: performing the heuristic algorithm using the expected data sequence and the fitness function to calculate the next optimal treatment which maximizes the wound change, and the next expected wound change value corresponding to the next optimal treatment, and then estimating the next expected data sequence using the expected data sequence and the next expected wound change value;

wherein the next expected data sequence is used as the new expected data sequence to iterate the second operation, until all of the size parameters in the next expected data sequence are calculated to be zero.

3. The wound multiple sensing method as claimed in claim 2, wherein the at least one size parameter is an expected wound length, an expected wound width, and an expected wound depth.

4. The wound multiple sensing method as claimed in claim 2, further comprising:

accumulating how many times the second operation is performed, until all of the size parameters in the next expected data sequence are calculated to be zero;

adding one to the number of times that the operation has been performed, and then multiplying this by cycle time during which the wound has been measured, so as to get an expected number of days required for the wound to heal.

5. The wound multiple sensing method as claimed in claim 1, wherein the wound change comprises three dimensions: a wound length change, a wound width change, and a wound depth change; and wherein maximizing the wound change comprises: maximizing a wound volume change; and wherein the expected wound change value comprises an expected wound length change value, an expected wound width change value, and an expected wound depth change value.

6. The wound multiple sensing method as claimed in claim 1, wherein each of the reference cases further comprises a characteristic record, a qualitative questionnaire record, and a treatment record;

wherein the case-data sequences are created based on the characteristic record; and wherein the similar case treatments are created based on the qualitative questionnaire record and the treatment record.

7. A wound multiple sensing system, comprising a processor configured to execute:

loading a plurality of reference cases, wherein each of the reference cases comprises a plurality of case-data sequences;

receiving a current wound characteristic of a wound, wherein the current wound characteristic comprises multiple items of wound-observation data;

creating a current data sequence based on the multiple items of wound-observation data;

calculating the similarity between the current data sequence and each of the case-data sequences in each of the reference cases;

selecting the case-data sequence which has the greatest similarity with the current data sequence, from the case-data sequences in each of the reference cases, to be a similar case-data sequence in each of the reference cases, wherein each similar case-data sequence is associated with a corresponding similar case treatment;

performing a multiple regression analysis using the similar case-data sequences and the similar case treatments to derive a fitness function, wherein the dependent variable of the fitness function is a wound change;

performing a heuristic algorithm using the current data sequence and the fitness function to calculate an optimal treatment which maximizes the wound change, and an expected wound change value corresponding to the optimal treatment;

wherein the wound multiple sensing system further comprises a wound device comprising:

a color sensor, configured to obtain wound-tissue data in the multiple items of wound-observation data;

a depth sensor, configured to obtain wound surface area data in the multiple items of wound-observation data; and a temperature sensor, configured to obtain wound-temperature data in the multiple items of wound-observation data.

8. The wound multiple sensing system as claimed in claim 7, wherein the processor further configured to execute:

a first operation: estimating the expected data sequence using the current data sequence and the expected wound change value, wherein the expected data sequence comprises at least one size parameter;

a second operation: performing the heuristic algorithm using the expected data sequence and the fitness function to calculate the next optimal treatment which maximizes the wound change, and the next expected wound change value corresponding to the next optimal treatment, and then estimating the next expected data sequence using the expected data sequence and the next expected wound change value;

wherein the next expected data sequence is used as the new expected data sequence to iterate the second operation, until all of the size parameters in the next expected data sequence are calculated to be zero.

9. The wound multiple sensing system as claimed in claim 8, wherein the at least one size parameter is the expected wound length, the expected wound width, and the expected wound depth.

10. The wound multiple sensing system as claimed in claim 8, wherein the processor further configured to execute:

accumulating how many times the second operation is performed, until all of the size parameters in the next expected data sequence are calculated to be zero;

adding one to the number of times that the operation has been performed, and then multiplying this by cycle time during which the wound has been measured, so as to get the expected number of days required for the wound to heal.

11. The wound multiple sensing system as claimed in claim 7, wherein the wound change comprises three dimensions: a wound length change, a wound width change, and a wound depth change; and wherein maximizing the wound change comprises: maximizing a wound volume change; and wherein the expected wound change value comprises the expected wound length change value, the expected wound width change value, and the expected wound depth change value.

12. The wound multiple sensing system as claimed in claim 7, wherein each of the reference cases further comprises a characteristic record, a qualitative questionnaire record, and a treatment record;

wherein the case-data sequences are created based on the characteristic record; and wherein the similar case treatments are created based on the qualitative questionnaire record and the treatment record.

* * * * *